United States Patent
Mountford

(10) Patent No.: US 11,346,909 B2
(45) Date of Patent: May 31, 2022

(54) SYSTEMS ARCHITECTURE FOR ANALYSIS OF SPECTROSCOPY AND FMRI DATA USING MULTIPLE INTEGRATED CLASSIFIERS

(71) Applicant: Translational Research Institute Pty Ltd as trustee for Translational Research Institute Trust, Woolloongabba (AU)

(72) Inventor: Carolyn Mountford, Robina (AU)

(73) Assignee: DatChem, Brisbane (AU)

( * ) Notice: Subject to any disclaimer, the term of this patent is extended or adjusted under 35 U.S.C. 154(b) by 338 days.

(21) Appl. No.: 16/736,184

(22) Filed: Jan. 7, 2020

(65) Prior Publication Data

US 2020/0217912 A1 Jul. 9, 2020

Related U.S. Application Data

(60) Provisional application No. 62/789,330, filed on Jan. 7, 2019.

(51) Int. Cl.
*G01R 33/46* (2006.01)
*A61B 5/00* (2006.01)
*G16H 40/67* (2018.01)
*A61B 5/055* (2006.01)
*G01R 33/54* (2006.01)
*G06F 17/14* (2006.01)

(52) U.S. Cl.
CPC ............ *G01R 33/46* (2013.01); *A61B 5/0022* (2013.01); *A61B 5/055* (2013.01); *A61B 5/4312* (2013.01); *A61B 5/4842* (2013.01); *A61B 5/7264* (2013.01); *G16H 40/67* (2018.01); *G01R 33/54* (2013.01); *G06F 17/141* (2013.01)

(58) Field of Classification Search
USPC ........................................................ 324/307
See application file for complete search history.

(56) References Cited

U.S. PATENT DOCUMENTS

| 9,764,162 B1 * | 9/2017 | Willcut ................ A61B 6/5294 |
| 2005/0129297 A1 | 6/2005 | Kamath et al. |
| 2008/0219932 A1 * | 9/2008 | Mountford ........... G01R 33/465 424/9.3 |

(Continued)

FOREIGN PATENT DOCUMENTS

| WO | 19980027865 A1 | 7/1998 |
| WO | 20180191824 A1 | 10/2018 |

OTHER PUBLICATIONS

International Search Report for copending PCT/IB2020/050095 dated Apr. 1, 2020 (5 pages).

(Continued)

*Primary Examiner* — Rodney E Fuller
(74) *Attorney, Agent, or Firm* — Lucas & Mercanti, LLP

(57) ABSTRACT

An integrated MRI and MRS system includes a plurality of different classifiers for detecting the likelihood of the new data to be one of the different diseases/conditions in different body organs, and even the progression of the disease, disease state and condition within that organ. An interface module receives information on the individual including region of the body and potential disease/condition; and provides this information to a data analysis unit which automatically dictates which coil, the scanning protocol and classifier.

37 Claims, 6 Drawing Sheets

(56) References Cited

U.S. PATENT DOCUMENTS

| | | |
|---|---|---|
| 2012/0245473 A1 | 9/2012 | Mycek et al. |
| 2013/0129168 A1 | 5/2013 | Ross |
| 2015/0182143 A1 | 7/2015 | Hirata et al. |
| 2018/0107798 A1* | 4/2018 | Hu .................. G06N 3/0454 |
| 2018/0204327 A1* | 7/2018 | Matthews ............ G16H 50/20 |

OTHER PUBLICATIONS

Written Opinion of the International Searching Authority for copending PCT/IB2020/050095 dated Apr. 1, 2020 (4 pages).

* cited by examiner

SYSTEMS ARCHITECTURE FOR ANALYSIS OF SPECTROSCOPY AND FMRI DATA USING MULTIPLE INTEGRATED CLASSIFIERS

CROSS-REFERENCE TO RELATED APPLICATIONS

The present application claims priority to U.S. Ser. No. 62/789,330, filed Jan. 7, 2019, which is incorporated by reference herein.

TECHNICAL FIELD

The present invention relates to a magnetic resonance (MR) system which is capable of providing data acquisition from a number of different bodily organs and a plurality of classifiers to enable medical personnel to provide diagnosis or the statistical likelihood of different conditions, diseases and disease states of the different diseases, for optimal therapy and treatment, all in a single integrated system, and method of using the system.

BACKGROUND OF THE INVENTION

Magnetic resonance imaging (MRI) and magnetic resonance spectroscopy (MRS) has been used to develop classifiers which enable trained medical personnel to diagnose different conditions and diseases in different organs, and even the disease state of progression of the disease within the organs, to guide in optimal therapy and treatment.

Such single-use classifiers are disclosed in U.S. Ser. No. 15/759,424 filed Mar. 12, 2018 entitled System and Method for Detecting and Monitoring Post Traumatic Stress Disorder (PTSD) using Magnetic Resonance Spectroscopy (MRS); U.S. Ser. No. 62/749,990 filed Oct. 24, 2018 entitled Functional Analysis Of Human Brain Using Functional Magnetic Resonance Imaging (fMRI) For Acute Stress And Post Traumatic Stress Disorder (PTSD) Monitoring Neuroplasticity; U.S. Ser. No. 62/711,986 filed Jul. 30, 2018 entitled Method and System For Detecting and Identifying Acute Stress Response From Traumatic Exposure, Its Transition To Post Traumatic Stress Disorder and Monitoring Subsequent Therapy; U.S. Ser. No. 62/694,258 filed Jul. 5, 2018 entitled Method and System For Detecting and Identifying Acute Pain, Its Transition To Chronic Pain, and Monitoring Subsequent Therapy; U.S. Ser. No. 14/775,909 filed Sep. 14, 2015 and U.S. Published Application No. 2016/0022197 published Mar. 17, 2016 entitled Detection of BRCA Carriers in Breast Tissue; U.S. Publication Application No. 2017/0172495 filed Mar. 18, 2015 entitled Method and System For Detecting and Identifying Different Types of Pain and Monitoring Subsequent Therapy; U.S. Publication Application No. 2008/0219932 filed Feb. 26, 2008 entitled Magnetic Resonance Spectroscopy of Breast Biopsy to Determine Pathology, Vascularization and Nodal Involvement; and U.S. Publication Application No. 2005/0020905 filed May 12, 2004 entitled System and Method For Detecting Pain and Its Components Using Magnetic Resonance Spectroscopy. These applications and publications are incorporated by reference herein.

These systems have been isolated and for single use because the classifiers have been stand-alone only for the particular condition, disease and organ.

SUMMARY OF THE INVENTION

In accordance with the invention, an integrated MRI and MRS system is provided which includes access to any one or more, or all, of a plurality of classifiers for detecting different conditions, and diseases in different body organs, and even the disease state of progression within that bodily organ. Such system enables a medical practitioner to obtain, with a single integrated system, data on the condition and disease state of patients without subjecting the patient to different systems for each condition, disease, and organ.

The system includes an interface module which receives information on the individual including a region of the body and a potential disease or condition for which spectroscopic data will be obtained. The interface module provides this information to a data analysis unit which automatically dictates which coil to use, the scanning protocol and which classifier(s) will be used to analyze the data. The system can automatically access the respective classifier, which may be stored locally on the system, or be stored at a remote location such as the cloud.

DETAILED DESCRIPTION OF THE PREFERRED EMBODIMENT

Figure 1:
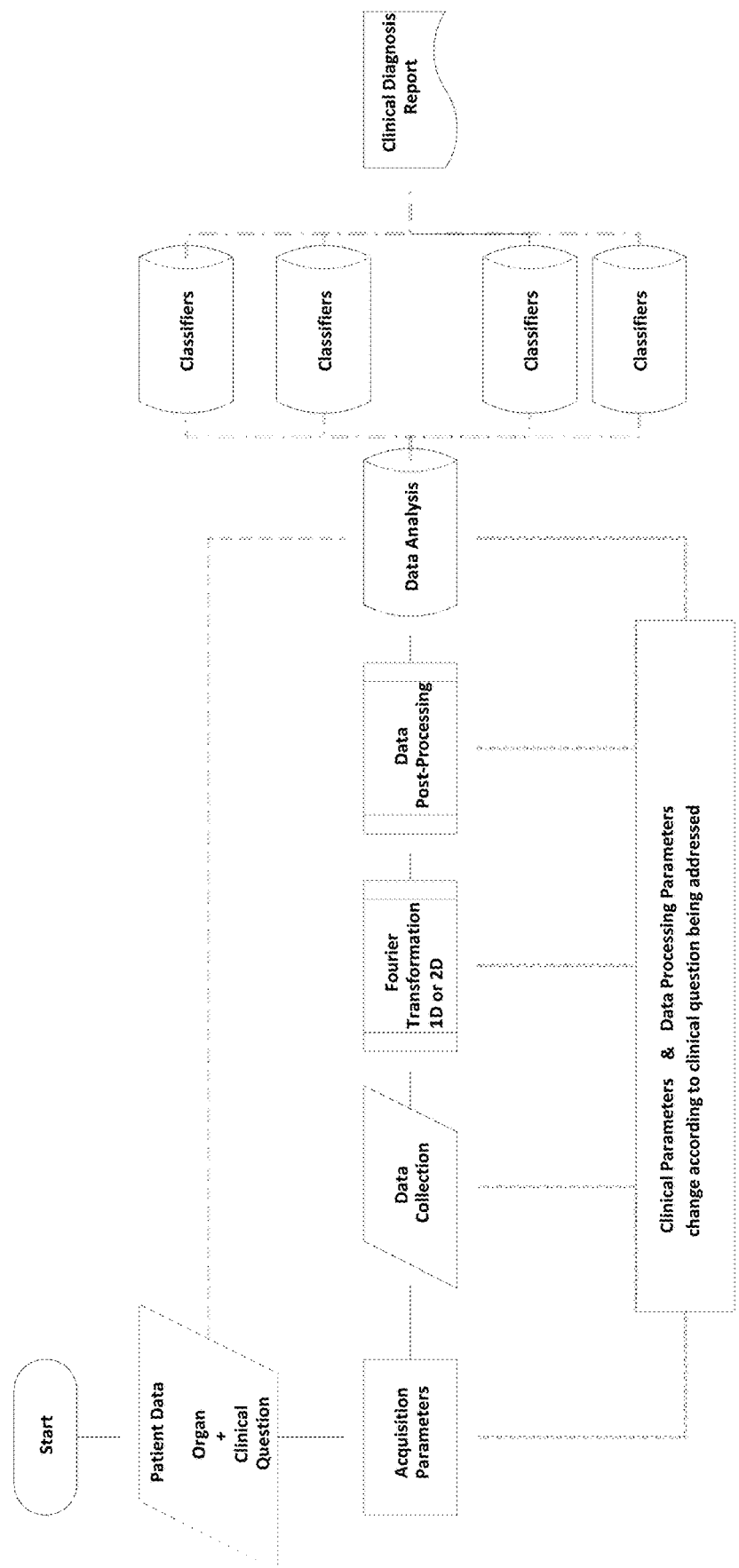
FIG. 1 is a block diagram of an integrated MR system which includes a data collection, Fourier transformation, data post processing and data analysis units, combined with an arrangement of an integrated MR system having a plurality of classifiers, each of which may be employed depending on the organ and disease/condition of interest. The integrated system has a plurality of classifiers, each of which may be employed at the selection of the operator or the instructions contained in an electronic referral. One or more of the system components, including one or more of the classifiers, may be located on a local server or cloud based server, optimally accessible over the Internet.

A preferred embodiment of a system and method will now be described, but the invention is not limited to this embodiment.

As used herein, the terms "disease", "disease state" and "condition" is all encompassing and is intended to include every abnormality of bodily disease, disease and condition, without limitation, as well as normal bodily states and conditions.

The present invention provides an automated system for enabling a practitioner to detect a plurality of disease states or conditions in an individual using magnetic resonance spectroscopy, comprising: an input module for receiving information on the individual including a region of the body and a potential disease or condition in that region for which spectroscopic data will be obtained; a magnetic resonance or spectroscopy scanner for obtaining spectroscopic data of the region of the body of the individual; and a plurality of classifiers, wherein at least one classifier is selected in response to the information received by the input module, the selected classifier receiving the spectroscopic data and comparing the spectroscopic data to reference data to enable a practitioner to provide a diagnosis of a disease state or condition of the region of the body of the individual, or the statistical likelihood that the disease or condition exists.

The input module may communicate to the operator operating parameters for obtaining the spectroscopic data in response to the information received by the interface module. The operating parameters may include pulse sequence and coil type used to obtain the spectroscopic data. The input module may include a bar code scanner, and at least some of the information on the individual received may be in bar code form. The disease state or condition may be a disease of the breast. The disease state or condition may be a condition of pain being experienced by the individual. The disease state or condition may be a neurological condition. The disease state or condition may cause neurochemical change as a consequence of the disease state or condition. The disease state or condition may be at least one of the presence of a BRCA mutation, a healthy breast, risk from family history and breast cancer. The condition may be at least one of acute pain and chronic pain. The neurological condition may be one of PTSD, acute anxiety and blast exposure. The disease state may be a disease of the ovary.

The spectroscopic data may be 1D MRS data. The spectroscopic data may be 2D COSY data. The system may further include a display for displaying a report of the diagnosis of the classifier. The system may further include a wavelet transformation unit. The system may further include a Fourier transformation unit, and a data post analysis unit. The plurality of classifiers may be located at a location remote from the spectroscopy scanner, and wherein the spectroscopic data is transmitted to the remote location. The plurality of classifiers may be located in the cloud.

The present invention provides an automated system for enabling a practitioner to detect a plurality of disease states or conditions in an individual using magnetic resonance spectroscopy, comprising: an input module for receiving information on the individual including a region of the body and a potential disease state or condition in that region for which spectroscopic data will be obtained; a MR scanner for obtaining spectroscopic data of the region of the body of the individual; a Fourier transformation unit to produce MRS data from the spectroscopy data; a data post post-processing spectrum module for evaluation of the MRS data, for enabling detection of disease state or condition; a wavelet transformation unit for receiving the spectroscopy data; a data post-processing unit, a data analysis unit for performing data analysis to identify discriminatory telltale markers sufficient to uniquely identify the disease state or condition, or the statistical likelihood that the disease state or condition exists; a plurality of classifiers, wherein at least one classifier is selected in response to the information received by the input module, the selected classifier receiving the data from the MBDA data analysis unit and comparing said last data to reference data to enable a practitioner to provide a diagnosis of a disease state or condition of the region of the body of the individual, or the statistical likelihood that the disease or condition exists.

The input module may communicate to the operator operating parameters for obtaining the spectroscopic data in response to the information received by the interface module. The system may perform a Fourier transformation and/or a wavelet transformation in response to a command from the input module. The operating parameters may include pulse sequence and coil type used to obtain the spectroscopic data. The input module may include a bar code scanner, and at least some of the information on the individual received may be in bar code form.

The disease state or condition may be a disease of the breast. The disease state or condition may be a condition of pain being experienced by the individual. The disease state or condition may be a neurological condition. The disease state or condition may cause neurochemical change as a consequence of the disease state or condition. The disease state or condition may be at least one of the presence of a BRCA mutation, a healthy breast, degree of risk from family history or breast cancer. The condition may be at least one of acute pain and chronic pain. The neurological condition may be one of PTSD, acute anxiety and blast exposure. The disease state may be a disease of the ovary.

The spectroscopic data may be 1D MRS data. The spectroscopic data may be 2D COSY data. The system may further include a display for displaying a report of the classifier of the data sent. The plurality of classifiers may be located at a location remote from the spectroscopy scanner, and the spectroscopic data may be transmitted to the remote location. The plurality of classifiers may be located in the cloud.

FIG. 1 is a block diagram of an integrated MR system which includes a data collection, Fourier transformation, and/or wavelet transformation using 1D or 2D data, data post processing and data analysis units, combined with a novel arrangement of an integrated MR system having a plurality of classifiers, each of which may be employed depending on the organ and disease/condition of interest.

FIG. 1 shows a system having a plurality of different classifiers for different diseases of different organs, and the disease states within that organ. The system can include all of the classifiers described in all of the other Figures, or may include only a subset of all the classifiers, depending on the particular need for the system for a special medical practice or specialty. The system of FIG. 1 includes an input module for inputting information such as patient data, one or more organs, diseases and/or conditions to be evaluated and other clinically relevant information for the particular patient. Based on the information inputted, the system determines the type of coil, protocol including what acquisition parameters and on which body organs the system will focus to obtain information for diagnosis, as well as which classifiers to which the resultant data will be compared. This information will then be provided to a data collection module or scanner to obtain the relevant scanning data for the organ and condition/disease.

The data obtained from the data acquisition can be handled in one of two ways.

Firstly, the data can be processed by Fourier transformation module to produce a 1D or 2D MRS, and/or wavelet transformation. The output of the Fourier transformation module and/or wavelet transformation will be provided to a data post-processing spectrum module for evaluation and reporting. Secondly the data can be sent to a data analysis module such as a magnetic resonance biomarker discovery algorithm (MBDA) where it will be Fourier or wavelet transformed and compared to a range of classifiers, selected depending on the organ and condition/disease state indicated by the patient clinical data inputted initially. An MBDA is one of several available methods for data mining spectral data and creating a classifier to distinguish several classes of medical conditions by locating and identifying one or more discriminatory data characteristics, such discriminatory biomarkers and their identifying spectral characteristics by which the presence and concentration of the biomarker indicates the statistical likelihood on whether a particular condition/disease exists and/or its state or progression.

Further information on developing classifiers may be found in references cited below, particularly reference (7) which also cites references (1-6), incorporated by reference herein, and reference (8). Optimally, the classifier will selectively identify the one or fewest highly discriminatory telltale markers sufficient to identify the disease/condition, or the statistical likelihood of the disease/condition. The classifiers and/or other system components can be located locally on a local server, or located remotely and accessed over a communication link such as the Internet and in the cloud on a cloud based server.

The classifiers can be any of the classifiers disclosed in the applications/publications cited above and incorporated by reference herein or others in preparation. The output of the classifier(s) selected will be provided in report form to the medical practitioner for evaluation. Because classifiers have been developed which are extremely robust and discriminatory, the output of the classifier provides highly reliable data on the statistical likelihood on whether a particular condition/disease exists and/or the state or progression of the disease state. The system can also be used to monitor the progress of different treatment or therapy which a patient is undergoing to see the rate of progress.

Figure 2:
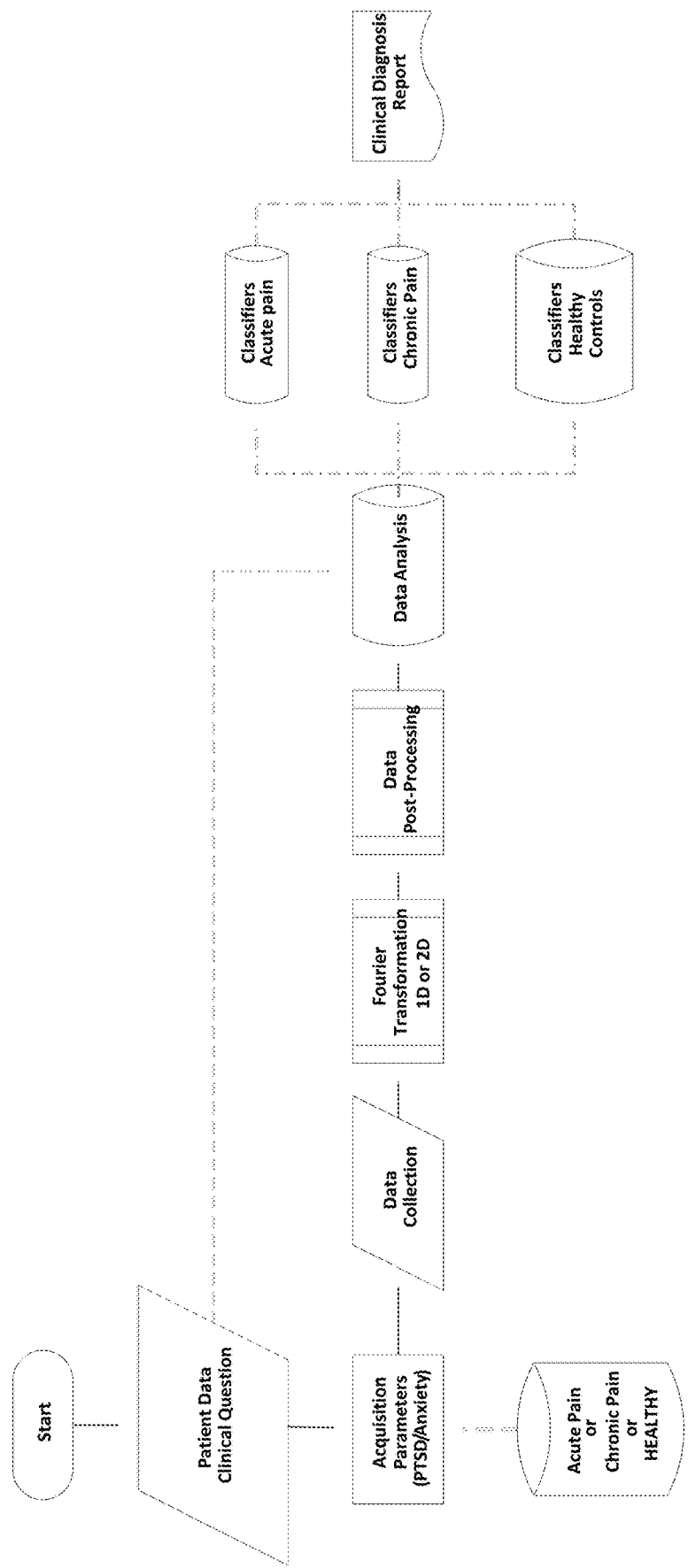
FIG. 2 is a block diagram similar to that of FIG. 1, but wherein a plurality of classifiers for breast cancer diagnosis are available for processing data specific to detect breast diseases and different levels of disease.

FIG. 2 is a block diagram of a system similar to that of FIG. 1, wherein the classifiers shown all relate to breast diseases and cancers, including detection of whether a patient has a mutation in a BRCA gene which would render them at increased risk of breast cancer relative to another patient not having the mutation; also to determine which women considered to be at risk due to a family history but at the time of examination have normal breast tissue determined by classifiers.

Figure 3:
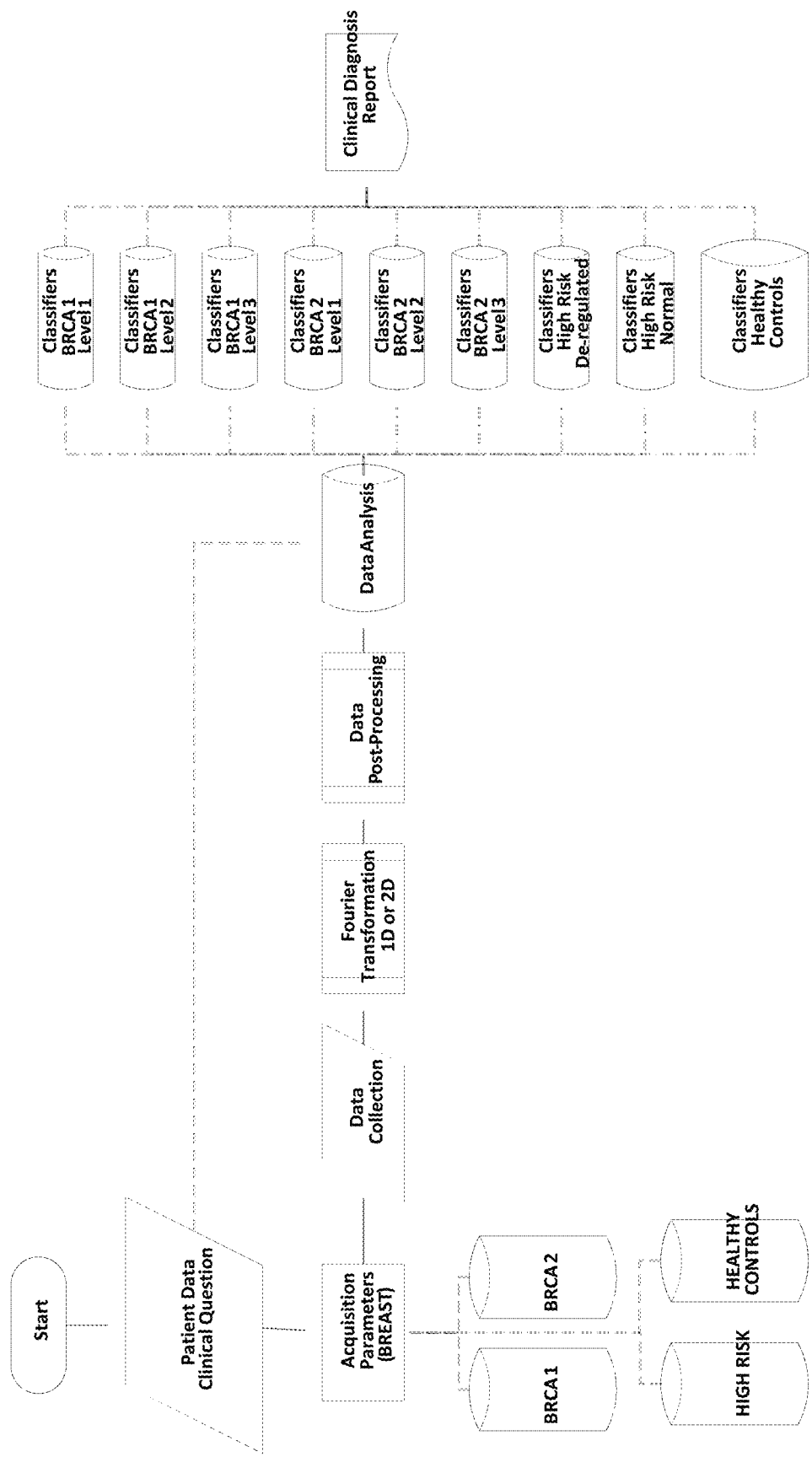
FIG. 3 is a block diagram of a system similar to that of FIG. 1, but wherein the plurality of classifiers designed for neurological conditions, such as post-traumatic stress disorder (PTSD), acute stress disorder (ASD), and blast exposure are available for different neurological disease states or conditions including the healthy brain.

FIG. 3 is a block diagram of a system similar to that of FIG. 1, wherein firstly the classifiers shown relate to detecting acute stress disorder which could include detecting whether a person has experienced an anxiety triggering event which could put them on a path towards acute stress disorder or PTSD if subjected to repeated anxiety or stress provoking events and not treated; secondly the person has or post-traumatic stress disorder (PTSD) and thirdly, the person has a suicide risk or tendency, or other condition in the mental health area. In this system, functional magnetic resonance imaging (fMRI) can be used to obtain the data used for the comparators and evaluation, as disclosed in U.S. Ser. No. 62/749,990 filed Oct. 24, 2018 entitled "Functional Analysis Of Human Brain Using Functional Magnetic Resonance Imaging (fMRI) For Acute Stress And Post Traumatic Stress Disorder (PTSD) Monitoring Neuroplasticity".

It should be understood that fMRI can be used instead of 2D COSY in any of the systems described herein.

Figure 4:
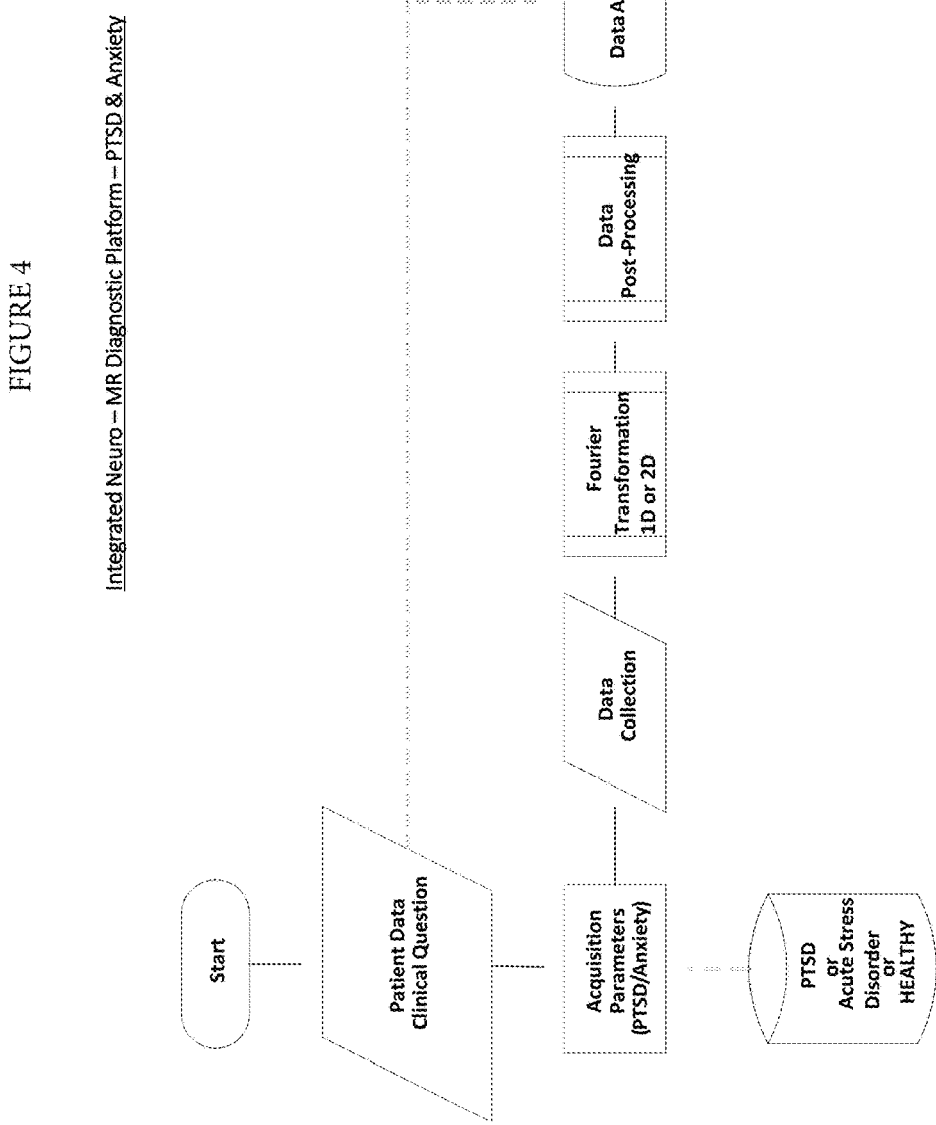
FIG. 4 is a block diagram of a system similar to that of FIG. 1, but wherein a plurality of classifiers designed for acute pain and chronic pain for different organs, are available for different pain conditions.

FIG. 4 is a block diagram of a system similar to that of FIG. 1, wherein the classifiers shown relate to detecting acute and chronic pain and a response to therapy or natural healing.

Figure 5:
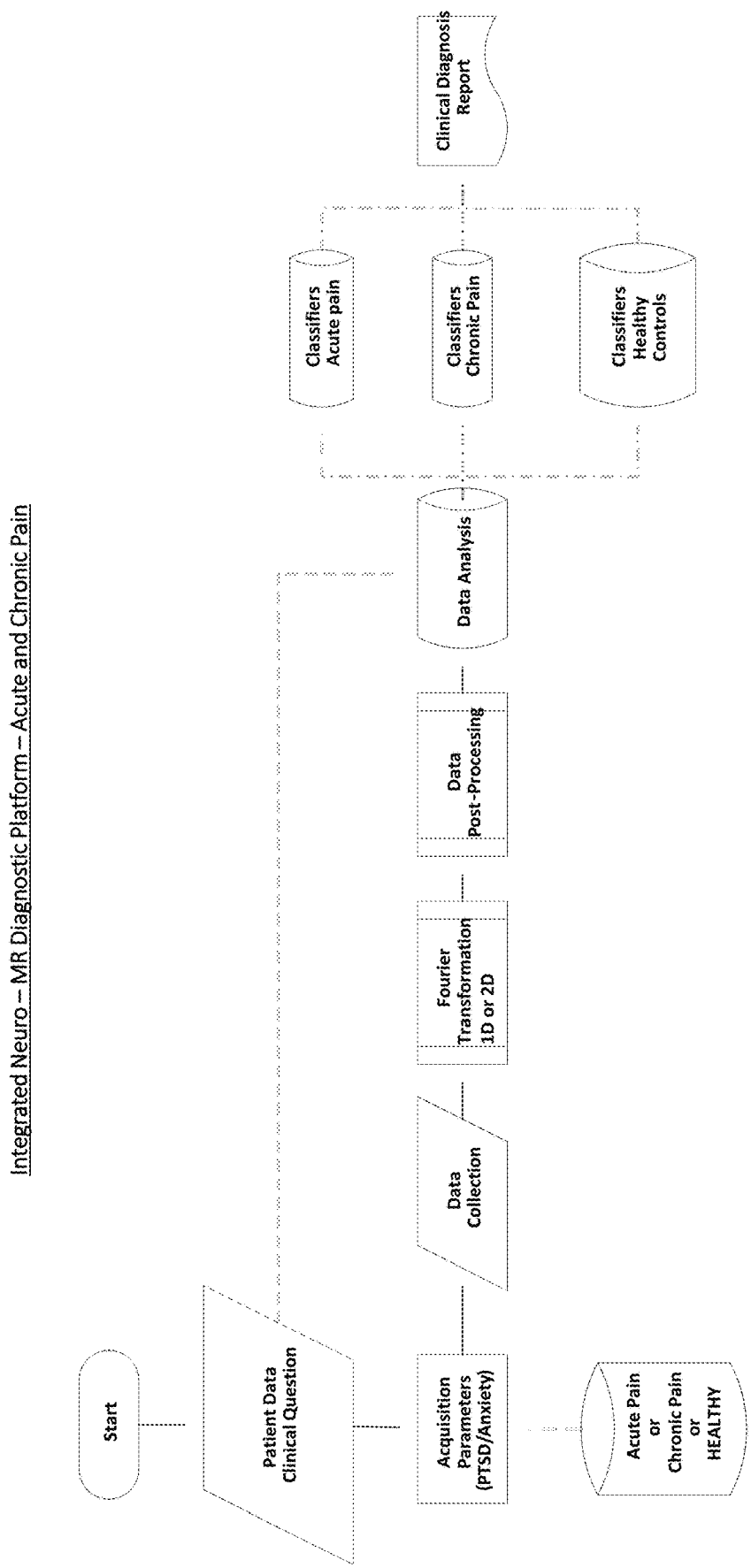
FIG. 5 is a block diagram of a system similar to that of FIG. 1 but wherein a plurality of classifiers for detecting diseases of the ovary are available.

FIG. 5 is a block diagram of a system similar to that of FIG. 1, wherein the classifiers detect diseases of the ovary.

In all cases of patient examination, the appropriate coils would be employed to obtain spectral data from the appropriate region or organ of the body. For breast data, the region or organ would be the breast. For acute stress disorder, PTSD, and acute and chronic pain or other mental health condition the appropriate region would be the brain using a head coil. For ovary it would be a body coil. The system would provide appropriate prompts to the operator of the system to alert operator to use the appropriate coil and pulse sequence. The system would automatically provide the appropriate classifier in response to the information initially inputted as to the region, organ, disease and/or condition of the individual undergoing evaluation. One, some or all of the classifiers may be available locally, or one, some or all may be accessed over a communication link at a remote location, such as the cloud, which would be password protected with local governance in place. By having the classifiers located elsewhere, they can be frequently refined and improved. Also, access could be controlled, so that access fees could be changed on a per access and use basis.

Figure 6:
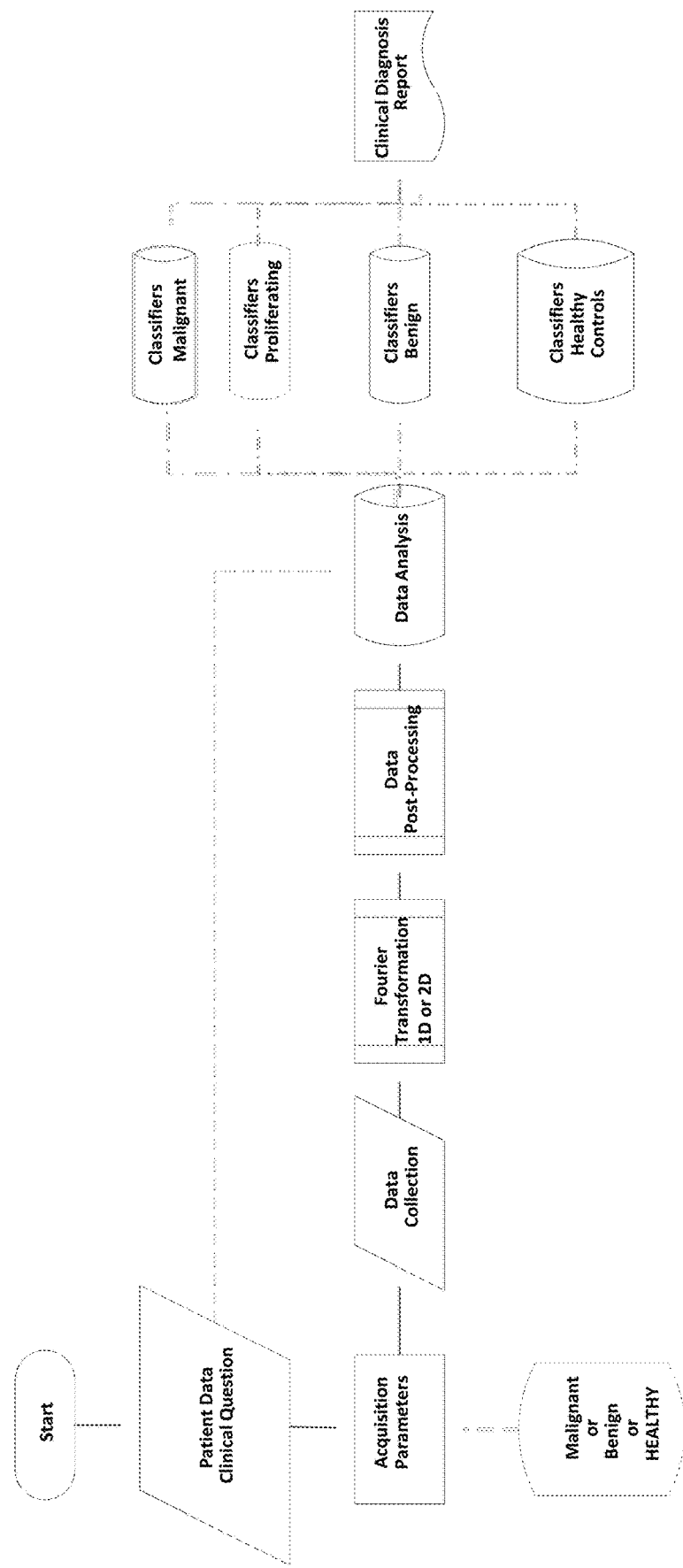
FIG. 6 shows a form suitable for recording the results of using the method and system for a patient.

The output of the data acquisition process could be provided on a form of the type shown in FIG. 6.

While several embodiments have been described, the invention is not limited to these embodiments, and the scope of the invention is defined only by way of the following claims.

REFERENCES CITED AND INCORPORATED BY REFERENCE

1. Ramadan S, Andronesi O C, Stanwell P, Lin A P, Sorensen A G, Mountford C E. Use of in vivo two-dimensional MR spectroscopy to compare the biochemistry of the human brain to that of glioblastoma. Radiology. 2011; 259(2):540-9.

2. Mountford C, Quadrelli S, Lin A, Ramadan S. Six fucose-alpha(1-2) sugars and alpha-fucose assigned in the human brain using in vivo two-dimensional MRS. NMR in biomedicine. 2015; 28(3):291-6.

3. Quadrelli S, Mountford C, Ramadan S. Hitchhiker's Guide to Voxel Segmentation for Partial Volume Correction of In Vivo Magnetic Resonance Spectroscopy. Magnetic resonance insights. 2016; 9:1-8.

4. Stanwell P, Siddall P, Keshava N, Cocuzzo D, Ramadan S, Lin A, et al. Neuro magnetic resonance spectroscopy using wavelet decomposition and statistical testing identifies biochemical changes in people with spinal cord injury and pain. Neuroimage. 2010; 53(2):544-52.

5. Cocuzzo D, Lin A, Ramadan S, Mountford C, Keshava N. Algorithms for characterizing brain metabolites in two-dimensional in vivo MR correlation spectroscopy. Conference proceedings: Annual International Conference of the IEEE Engineering in Medicine and Biology Society IEEE Engineering in Medicine and Biology Society Annual Conference. 2011; 2011:4929-34.

6. Cocuzzo D, Lin A, Stanwell P, Mountford C, Keshava N. In Vivo Brain Magnetic Resonance Spectroscopy: A Measurement of Biomarker Sensitivity to Post-Processing Algorithms. IEEE Journal of Translational Engineering in Health and Medicine. 2014; 2:1-17.

7. Mountford C, MRS as a Biomarker for Brain Disease, Proc. Intl. Soc. Mag. Med. 25 (2017)

8. Tosh N, Quadrelli S, Galloway G, Mountford C, Two New Fucose-α (1-2)-Glycans Assigned In The Healthy Human Brain Taking The Number To Seven. Scientific Reports 9, Article number: 18806 (2019)

9. Quadrelli S, Tosh N, Urqhart A, Trickey K, Tremewan R, Galloway G, Rich L, Lea R, Malycha P, Mountford C, Post-traumatic stress disorder affects fucose-α (1-2)-glycans in the human brain: preliminary findings of neuro deregulation using in vivo two-dimensional neuro MR spectroscopy.

The invention claimed is:

1. An automated system for enabling a practitioner to detect a plurality of disease states or conditions in an individual using magnetic resonance spectroscopy, comprising:
   an input module for receiving information on the individual including a region of the body and a potential disease, disease state or condition in that region for which spectroscopic data will be obtained;
   a magnetic resonance or spectroscopy scanner for obtaining spectroscopic data of the region of the body of the individual; and
   a plurality of classifiers, wherein at least one classifier is selected in response to the information received by the input module, the selected classifier receiving the spectroscopic data and comparing the spectroscopic data to reference data to enable a practitioner to provide a diagnosis of a disease, disease state or condition of the region of the body of the individual, or the statistical likelihood that the disease, disease state or condition exists.

2. The system of claim 1, wherein the input module communicates to the operator operating parameters for obtaining the spectroscopic data in response to the information received by the interface module.

3. The system of claim 2, wherein the operating parameters include pulse sequence and coil type used to obtain the spectroscopic data.

4. The system of claim 1, wherein the input module includes a bar code scanner, and at least some of the information on the individual received is in bar code form.

5. The system or claim 4, wherein the disease, disease state or condition is at least one of the presence of a BRCA mutation, a healthy breast, degree of risk from family history and breast cancer.

6. The system of claim 1, wherein the disease, disease state or condition is a disease of the breast.

7. The system of claim 6, wherein the disease, disease state or condition is a condition of pain being experienced by the individual.

8. The system of claim 7, wherein the condition is at least one of acute pain and chronic pain.

9. The system of claim 1, wherein the disease, disease state or condition is a neurological condition.

10. The system of claim 9, wherein the neurological condition is one of PTSD, acute anxiety and blast exposure.

11. The system of claim 1, wherein the disease, disease state or condition causes neurochemical change as a consequence of the disease, disease state or condition.

12. The system of claim 1, wherein the disease or disease state is a disease or disease state of the ovary.

13. The system of claim 1, wherein the spectroscopic data is 1D MRS data.

14. The system of claim 1, wherein the spectroscopic data is 2D COSY data.

15. The system of claim 1, further including a display for displaying a report of the diagnosis of the classifier.

16. The system of claim 1, further including a wavelet transformation unit.

17. The system of claim 1, further including a Fourier transformation unit, a data post analysis unit.

18. The system of claim 1, wherein the plurality of classifiers is located at a location remote from the spectroscopy scanner, and wherein the spectroscopic data is transmitted to the remote location.

19. The system of claim 1, wherein the plurality of classifiers is located in the cloud.

20. An automated system for enabling a practitioner to detect a plurality of diseases, disease states or conditions in an individual using magnetic resonance spectroscopy, comprising:
   an input module for receiving information on the individual including a region of the body and a potential disease, disease state or condition in that region for which spectroscopic data will be obtained;
   a MR scanner for obtaining spectroscopic data of the region of the body of the individual;
   a Fourier transformation unit to produce MRS data from the spectroscopy data;
   a data post post-processing spectrum module for evaluation of the MRS data, for enabling detection of disease, disease state or condition;
   a wavelet transformation unit for receiving the spectroscopy data;
   a data post-processing unit for performing data analysis to identify discriminatory telltale markers sufficient to uniquely identify the disease, disease state or condition, or the statistical likelihood that the disease, disease state or condition exists;
   a plurality of classifiers, wherein at least one classifier is selected in response to the information received by the input module, the selected classifier receiving the data from the post-processing unit and comparing said last data to reference data to enable a practitioner to provide a diagnosis of a disease, disease state or condition of the region of the body of the individual, or the statistical likelihood that the disease, disease state or condition exists.

21. The system of claim 20, wherein the input module communicates to the operator operating parameters for obtaining the spectroscopic data in response to the information received by the interface module.

22. The system of claim 21, wherein the operating parameters include pulse sequence and coil type used to obtain the spectroscopic data.

23. The system of claim 20, wherein system performs a Fourier transformation and/or a wavelet transformation in response to a command from the input module.

24. The system of claim 20, wherein the input module includes a bar code scanner, and at least some of the information on the individual received is in bar code form.

25. The system of claim 20, wherein the disease, disease state or condition is a disease of the breast.

26. The system of claim 25, wherein the disease, disease state or condition is a condition of pain being experienced by the individual.

27. The system of claim 26, wherein the condition is at least one of acute pain and chronic pain.

28. The system of claim 20, wherein the disease, disease state or condition is a neurological condition.

29. The system of claim 28, wherein the neurological condition is one of PTSD, acute anxiety and blast exposure.

30. The system of claim 20, wherein the disease, disease state or condition causes neurochemical change as a consequence of the disease, disease state or condition.

31. The system or claim 20, wherein the disease, disease state or condition is at least one of the presence of a BRCA mutation, a healthy breast, degree of risk from family history or breast cancer.

32. The system of claim 20, wherein the disease or disease state is a disease of the ovary.

33. The system of claim 20, wherein the spectroscopic data is 1D MRS data.

34. The system of claim 20, wherein the spectroscopic data is 2D COSY data.

35. The system of claim 20, further including a display for displaying a report of the classifier of the data sent.

36. The system of claim 20, wherein the plurality of classifiers is located at a location remote from the spectroscopy scanner, and wherein the spectroscopic data is transmitted to the remote location.

37. The system of claim 20, wherein the plurality of classifiers is located in the cloud.

* * * * *